United States Patent [19]

Shinohara et al.

[11] 4,209,377

[45] Jun. 24, 1980

[54] OXYGEN SENSING ELEMENT

[75] Inventors: Hiroshi Shinohara, Okazaki; Yasuhiro Otsuka, Toyota; Shinichi Matsumoto, Toyota; Toshinobu Furutani, Toyota; Hiroshi Wakizaka, Toyota, all of Japan

[73] Assignee: Toyota Jidosha Kogyo Kabushiki Kaisha, Toyota, Japan

[21] Appl. No.: 27,832

[22] Filed: Apr. 6, 1979

[30] Foreign Application Priority Data

Sep. 8, 1978 [JP] Japan .................................. 53-110305

[51] Int. Cl.$^2$ ............................................ G01N 27/58
[52] U.S. Cl. ............................................... 204/195 S
[58] Field of Search ............... 204/195 S, 1 S; 422/98; 324/29

[56] References Cited

U.S. PATENT DOCUMENTS

| | | | |
|---|---|---|---|
| 3,904,486 | 9/1975 | Faurschou et al. | 204/1 T |
| 3,915,830 | 10/1975 | Isenberg | 204/195 S |
| 4,096,048 | 6/1978 | Matsumoto et al. | 204/195 S |
| 4,141,812 | 2/1979 | Kawawa et al. | 204/195 S |

*Primary Examiner*—G. L. Kaplan
*Attorney, Agent, or Firm*—Kenyon & Kenyon

[57] ABSTRACT

The high temperature durability of an oxygen sensing element, which comprises a solid electrolyte member composed of sintered material, and a means for providing a reference oxygen partial pressure, composed of a sintered product of a finely divided metal or metal-metal oxide mixture powder and being completely embedded within the solid electrolyte member, is improved by incorporating in the finely divided metal or metal-metal oxide mixture powder an antisintering material and a pore-forming material capable of subliming or being decomposed, thereby to generate gas upon sintering. The amounts of the antisintering material and the pore-forming material are from 5 to 70% by weight and from 20 to 80% by weight, respectively, based on the total weight of these additives-incorporated metal or metal-metal oxide mixture. The low temperature operation capability of the oxygen sensing element is improved by further incorporating therein a minor amount of a platinum group metal.

7 Claims, 5 Drawing Figures

OXYGEN SENSING ELEMENT

BACKGROUND OF THE INVENTION

This invention relates to an oxygen sensing element capable of measuring partial pressures of oxygen in sample gases. More particularly, it relates to an oxygen sensing element suitable for use in an exhaust gas purifying system wherein the content of oxygen in an exhaust gas from an automobile internal combustion engine is measured, thereby to determine the content of unburnt hydrocarbons, carbon monoxide and nitrogen oxides in the exhaust gas and, based on the measurement results, the air-fuel ratio is appropriately adjusted so that the efficiency of a catalyst, for purifying the exhaust gas is enhanced; or suitable for use in a device for measuring the concentration of oxygen in a molten metal in the course of metal refining.

An oxygen sensor is an oxygen concentration cell having a structure such that electrodes are mounted on the opposite sides of a solid electrolyte composed of a sintered ceramic material capable of conducting an oxygen ion. An electromotive force is produced across the solid electrolyte by the difference between the partial pressures of oxygen in reference and sample gases contacting opposite sides of the solid electrolyte. The concentration of oxygen in the sample gas can be determined by measuring the electromotive force so produced. That is, as is well known, assuming that the partial pressures of oxygen in the reference and sample gases are $PO_2(1)$ and $PO_2(2)$, respectively, the electromotive force E produced between the electrodes on the opposite sides of the solid electrolyte is expressed by the following equation.

$$E = \frac{RT}{4F} \ln \frac{PO_2(1)}{PO_2(2)}$$

wherein R is gas constant, T is absolute temperature and F is Faraday's constant. Thus, if the partial pressure of oxygen $PO_2(1)$ in the reference gas is known, the partial pressure of oxygen $PO_2(2)$ in the sample gas can be determined from the above-mentioned equation by measuring the electromotive force E. Conventionally, air is used as the reference gas. The reference gas may also be generated chemically by using a mixture of a metal and its oxide which produces an equilibrium partial pressure of oxygen. This reference gas-generating metal-metal oxide mixture is hereinafter referred to as "reference solid electrode" for brevity.

However, the conventional oxygen sensors, wherein the reference solid electrode of a metal-metal oxide mixture is employed, are not advantageous compared with the oxygen sensors wherein air is used as the reference gas. This is because the former oxygen sensors do not successfully operate at a low temperature. That is, at a temperature lower than about 400° C., the former oxygen sensors generate little or no electromotive force and the internal impedance thereof is undesirably increased together with an apparent reduction of the electromotive force. In order to overcome this defect, it has been proposed to provide an electrode layer on the interface between the metal-metal oxide mixture reference solid electrode and the solid electrolyte, which electrode layer is composed of an electrochemically active metal such as platinum. The electrode layer accelerates the conversion of oxygen ions to molecular or atomic oxygen according to the following formula and, thus, reduces the polarization occurring in the metal-metal oxide mixture.

$$2O^{--} \rightarrow O_2 \text{ (or } 2O\text{)} + 4e^-$$

Such an electrode layer is formed by chemical or electrical plating, ion-plating or the like. However, the formation of such an electrode layer is complicated, and it is difficult to avoid a variability of some performances such as the operating temperature, the response time and the internal resistance among the resulting oxygen sensors.

Japanese Patent Publication (KOKAI) No. 9497/1976 discloses an oxygen sensing electrochemical cell having a structure such that a reference medium of a metal-metal oxide mixture is completely enclosed within a solid electrolyte member having an electrode mounted on the exterior surface thereof. This oxygen sensing electrochemical cell does not have such a defect as is encountered in the above-metioned oxygen sensing cell provided with an electrochemically active metal electrode layer on the interface between the metal-metal oxide mixture reference solid electrode and the solid electrolyte. This cell is, however, still not satisfactory in its operability at a low temperature.

In addition, the conventional oxygen sensors, which are composed of a reference solid electrode, a solid electrolyte and, optionally, an electrochemically active metal electrode layer on the interface between the reference solid electrode and the solid electrolyte, have the following defects. That is, these oxygen sensors are liable to be distorted or cracked, and on occasion the metal electrode layer is separated from the reference solid electrode and/or the solid electrolyte, during the high temperature operation of these sensors or during the step of sintering these sensors in the course of their manufacture. These defects lead to a reduction in the responsiveness of the oxygen sensors.

SUMMARY OF THE INVENTION

The main object of the present invention is to provide improved oxygen sensing elements which are neither distorted nor cracked, and metal electrodes which are not separated therefrom, during the step of sintering the oxygen sensing elements in the course of their manufacture or during the high temperature operation thereof.

Another object of the present invention is to provide improved oxygen sensing elements which exhibit a satisfactory low temperature operability and are capable of being manufacturing without a substantial variability of performances among the resulting oxygen sensing elements.

Other objects and advantages of the present invention will be apparent from the following description.

In accordance with the present invention, there is provided an improvement in an oxygen sensing element which comprises a solid electrolyte member composed of sintered material, and a means for providing a reference partial pressure of oxygen, composed of a sintered product of a finely divided metal or metal-metal oxide mixture powder; the reference oxygen partial pressure-providing means being completely embedded within the solid electrolyte member and having a lead-out wire connected thereto, and the solid electrolyte member having an electrode or electrodes mounted on the exterior surface thereof. The improvement of the present invention resides in the fact that the metal or metal-metal oxide mixture powder used for the preparation of the reference oxygen partial pressure-providing means has dispersed therein an antisintering material and a pore-forming material capable of subliming or being decomposed, thereby to generate gas upon sintering; the amounts of the antisintering material and the pore-forming material being from 5 to 70% by weight and from 20 to 80% by weight, respectively, based on the total weight of the antisintering and pore-forming materials-incorporated metal or metal-metal oxide mixture powder.

BRIEF DESCRIPTION OF THE DRAWINGS

The invention will be described in detail by way of examples with reference to the accompanying drawings in which.

DETAILED DESCRIPTION OF THE EMBODIMENT

Figure 1:
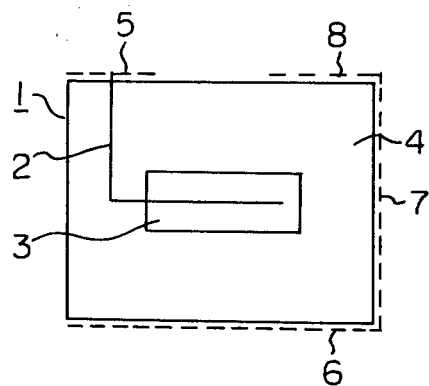
FIG. 1 is a schematic section of an embodiment of the oxygen sensing element of the invention.

Referring to FIG. 1, there is illustrated a schematic section of an embodiment of the oxygen sensing element of the invention. THe oxygen sensing element 1 has a means 3 for providing a reference partial pressure of oxygen, composed of a sintered body of a finely divided metal or metal-metal oxide mixture powder, (i.e., a reference solid electrode). The reference solid electrode 3 is totally embedded within a solid electrolyte member 4, and has an electrode lead-out wire 2 connected thereto, made of a thermally resistant electroconductive metal such as platinum or a platinum-rhodium alloy. The solid electrolyte member 4 has metal electrodes 5 and 6 on the exterior surface thereof. The electrode 5 is an auxiliary electrode for transmitting therethrough an output signal from the reference solid electrode 3 to an electrical measuring circuit (not shown in FIG. 1). The electrode 6 is a porous metal electrode to be exposed to a sample gas. Electrode lead 7-8 is intended to transmit therethrough an output signal from the electrode 6 to the electrical measuring circuit. The oxygen sensing element 1 may be of any desired shape, such as, for example, a disc, column, sphere or parallelopiped. Of these, a disc and column are desirable.

The solid electrolyte member 4 may be composed of a solid electrolyte material conventionally used in oxygen concentration cells, such as zirconia ($ZrO_2$). The solid electrolyte material is preferably a solid solution prepared by incorporating a minor amount of $Y_2O_3$, CaO or MgO followed by sintering. An optimum solid electrolyte material is comprised of a sintered zirconia composition having incorporated therein 5 to 10% by mole of $Y_2O_3$.

The reference solid electrode 3 is a sintered product of a finely divided metal or metal-metal oxide mixture powder. Even when the reference solid electrode is not made of a metal-metal oxide mixture but only metal, it can provide a reference partial pressure of oxygen, because the reference solid electrode accepts oxygen ions transmitted through the solid electrolyte material during the operation of the oxygen sensing element and, thus, the metal is partially converted into metal oxide. The metal ingredients used for the preparation of the reference solid electrode include, for example, iron, molybdenum, chromium, tungsten, nickel, cobalt, silicon and manganese.

The reference solid electrode 3 employed in the oxygen sensing element of the invention is characterized as being composed of the sintered product of a finely divided metal or metal-metal oxide mixture composition having incorporated therein an antisintering material and a pore-forming material capable of subliming or being decomposed, thereby to generate gas upon sintering. The amount of the antisintering material is from 5 to 70% by weight, preferably from 10 to 60% by weight, based on the total weight of the antisintering and pore-forming materials-incorporated metal or metal-metal oxide mixture composition. When the amount of the antisintering material is less than about 5% by weight, the reference solid electrode composition is liable to be excessively sintered and the resulting oxygen sensor becomes poor in high temperature durability. In contrast, when the amount of the antisintering material exceeds about 70% by weight, the resulting oxygen sensor is poor in electromotive force and service life. The desired effect of the antisintering material is prominent particularly when the reference solid electrode base composition is composed of an iron or iron-iron oxide mixture.

The antisintering material used includes, for example, stabilized zirconia ($ZrO_2$), which is usually identical to that used for the solid electrolyte material, and alumina ($Al_2O_3$) alumina-magnesia ($Al_2O_3$, MgO), silica ($SiO_2$) and alumina-silica ($Al_2O_3$-$SiO_2$). These antisintering materials may be used either alone or in combination.

The pore-forming material used in addition to the antisintering material is solid under normal conditions but is capable of subliming or being decomposed, thereby to generate or be converted to gas when heated in the sintering step. Thus, the pore-forming material produces innumerable pores in the sintered product. By the incorporation of the pore-forming material, the thermal expansion or contraction of the reference solid electrode can be made to be the same as that of the solid electrolyte. Thus, the oxygen sensing element is will not be distorted in the sintering step, and its high temperature durability increases. The pore-forming material includes, for example, ammonium bicarbonate, naphthalene and camphor. These pore-forming materials may be used either alone or in combination. The amount of the pore-forming material may appropriately be varied, depending upon the particular pore-forming material, the metal or metal-metal oxide mixture of the reference solid electrode and the solid electrolyte. For example, the amount of ammonium bicarbonate is preferably from 30 to 50% by weight. In general the amount of the pore-forming material is in the range of from 20 to 80% by weight based on the total weight of the antisintering and pore-forming materials-incorporated metal or metal-metal oxide mixture.

The main point of the present invention resides in the combined use of the antisintering material and the pore-forming material. By this combined use, the high temperature durability of the oxygen sensing element is increased to a great extent as compared with the single use of either one of the two materials.

Figure 3:
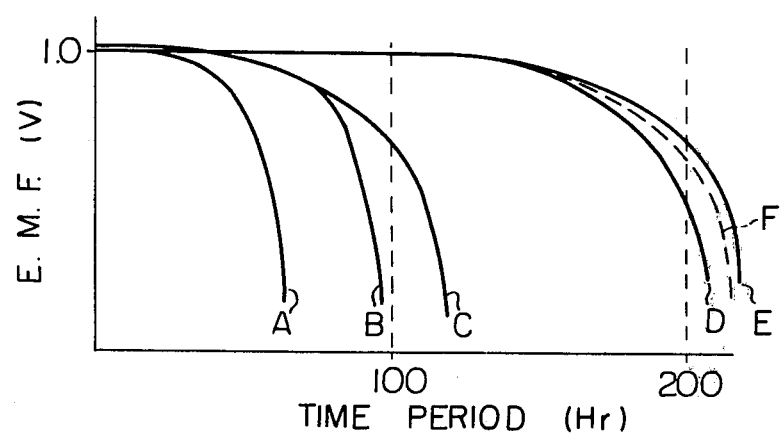
FIG. 3 is a graph showing the dependence of the electromotive force (E.M.F.) of oxygen sensing elements upon the operating period.

Referring to FIG. 3, there is disclosed a graph showing the durability of oxygen sensing elements, i.e. the dependence of the electromotive force (E.M.F.) upon the period of operation. The ordinate and the abscissa represent the E.M.F. in volts and the period of operation in hours, respectively. In FIG. 3, curves A, B, C, D, E and F were plotted from data obtained from the oxygen sensing element specimens having the following reference solid electrodes, respectively, under the conditions mentioned in Example 2, below.

A: Neither antisintering material nor pore-forming material incorporated.
B: Only pore-forming material incorporated.
C: Only antisintering material incorporated.
D, E and F: Both antisintering material and pore-forming material incorporated.

The E.M.F. decreased to 0.5 volt when the comparative oxygen sensing elements B and C were operated for approximately 100 hours. In contrast, the E.M.F. decreased to 0.5 volt when the oxygen sensing elements of the invention D, E and F were operated for 200 hours or more.

The reference solid electrode may preferably contain, in addition to the metal or metal-metal oxide mixture, the antisintering material and the pore-forming material, a minor amount of a platinum group metal. It is presumed that the platinum group metal dispersed in the reference solid electrode catalytically accelerates the electrode reaction, i.e., the conversion of oxygen ions, transmitted through the solid electrolyte, into molecular or atomic oxygen due to the oxidative effect of the metal constituting the reference solid electrode. Thus, the oxygen sensing element exhibits a reduced internal impedance and a good low temperature operability, which are comparable with or more satisfactory than those of the conventional oxygen sensing element having an electrode layer of an electrochemically active metal on the interface between the reference solid electrode and the solid electrolyte. Furthermore, the oxygen sensing element having the reference solid electrode having dispersed therein a platinum group metal has a simple structure and exhibits little or no variability of performances such as the operating temperature, the response time and the internal resistance.

The amount of the platinum group metal is from 0.5 to 10% by weight, preferably from 1.0 to 5.0% by weight, based on the total weight of the reference solid electrode composition. When the amount of the platinum group metal is less than about 0.5% by weight, the intended purpose cannot be achieved. In contrast, when the amount of the platinum group metal exceeds about 10% by weight, the manufacturing cost increases, and both the reduction of the internal impedance and the improvement of the low temperature operability are not in proportion to the increase in the amount of the incorporated platinum group metal. The platinum group metal includes, for example, platinum, rhodium, palladium and iridium. These metals may be used either alone or in combination. Of these metals platinum is preferable. A mixture of from 1.0 to 5.0% by weight of platinum, and not more than 2.0% by weight, particularly from 0.1 to 0.5% by weight, of rhodium is more preferable.

The oxygen sensing element of the present invention is manufactured in various ways. For example, a finely divided metal or metal-metal oxide mixture powder having incorporated therein predetermined amounts of antisintering material, pore-forming material and optional platinum group metal is press-molded to form a reference solid electrode. Then, the reference solid electrode is encapsulated within a solid electrolyte member by forming the solid electrolyte member on the exterior surface of the reference solid electrode by vapor deposition, ion plating, sintering and sputtering, as disclosed in Japanese Patent Publication (KOKAI) No. 9497/1976. Finally, the so formed product is sintered.

In another more preferable technique, a part of the amount of a finely divided solid electrolyte material, required for the formation of the solid electrolyte member is press-molded to form a provisional solid electrolyte member having a hole in which a reference solid electrode is to be formed. Then, a predetermined amount of the reference solid electrode composition is charged in the hole of the provisional solid electrolyte member followed by pressing the charged composition. In the recess of the provisional solid electrolyte member, formed by the pressing of the charged composition, the remaining part of the finely divided solid electrolyte material is heaped up. Then the heaped up material is pressed to obtain a structure such that the reference solid electrode is completely encapsulated or embedded within the solid electrolyte member. Lead wire or wires may be fitted to the so obtained structure or to an intermediate molded product formed in the above-mentioned course of manufacture. Finally, the obtained structure is sintered in a non-oxidizing atmosphere at a temperature of from about 1,400° to about 1,450° C. for a period of from 3 to 5 hours.

The mounting of the external electrode to be exposed to a sample gas and auxiliary electrode and electrode leads on the exterior surface of the solid electrolyte member may be carried out by a conventional technique such as paste coating and baking, electrical or chemical plating or ion plating by using a thermal-resistant conductive material such as platinum or a platinum-rhodium alloy. It is preferable that the porous external electrode 6 (FIG. 1) to be exposed to a sample gas be coated with a porous layer having a magnesium spinel structure or another spinel structure composed of a thermal resistant metal oxide. Such a porous layer may be formed by a conventional technique, such as a flame spraying technique. The porous layer minimizes the deterioration of the porous external electrode caused by the phosphorus, lead and sulfur present in the exhaust gas from an automobile.

As explained above, the oxygen sensing element of the invention is generally manufactured by a process wherein the reference solid electrode material and the solid electrolyte material embedded in the reference solid electrode material are simultaneously sintered. Thus, a part of the reference solid electrode material is dispersed in the solid electrolyte material in the proximity of the interface between the two materials, which results in the electrical contact of the two materials being reliable and durable. Therefore, the oxygen sensing element of the present invention exhibits a reduced internal impedance and a satisfactory low temperature operability without the provision of an electrochemically active metal electrode layer on the interface between the above-mentioned two materials. Furthermore, the combined incorporation of the antisintering material and the pore-forming material improves the high temperature durability. In addition, the oxygen sensing element of the invention has a simple structure which is easy to manufacture, and it exhibits little or no variability of performances such as the operating temperature, the response time and the internal resistance.

The oxygen sensing element of the invention is advantageously used for measuring the content of oxygen, for example, in an exhaust gas from an automobile internal combustion engine or in a molten metal in the course of metal refining. It is particularly suitable for use in an exhaust gas purifying system wherein the content of oxygen in an exhaust gas from an automobile internal cimbustion engine is measured, thereby to determine the content of unburnt hydrocarbons, carbon monoxide and nitrogen oxides in the exhaust gas, and based on the measurement results, the air-fuel ratio is appropriately adjusted so that the efficiency of a catalyst for purifying the exhaust gas is enhanced.

Figure 2A:
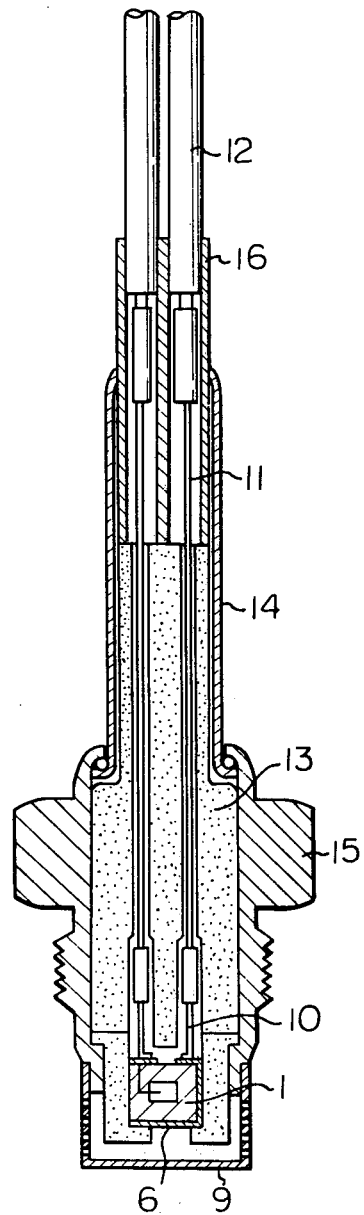
FIGS. 2A and 2B are a vertical section and a partial section side elevation, respectively, of an embodiment of the oxygen sensor device for use in automobiles.
Figure 2B:
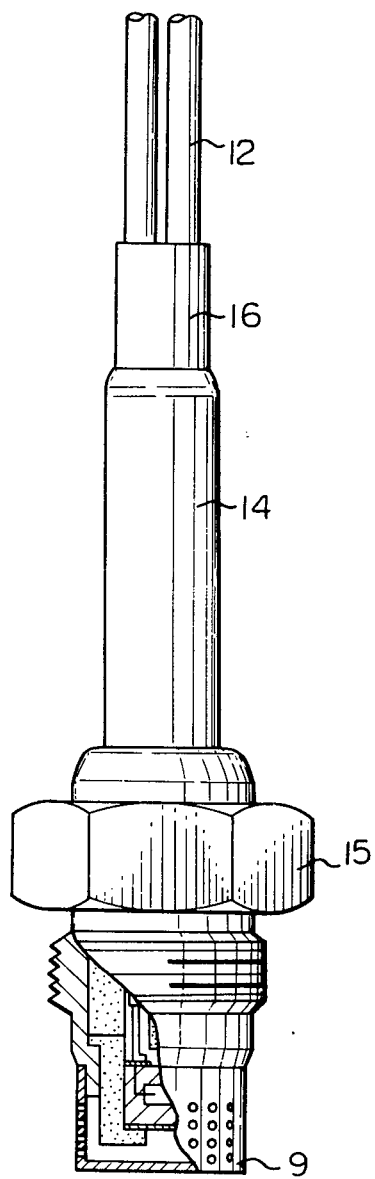

Referring to FIGS. 2A and 2B is disclosed an embodiment of the oxygen sensor device useful for measuring the content of oxygen in an exhaust gas from an automobile internal combustion engine. The oxygen sensor device is fitted to the exhaust manifold in a manner such that the external platinum electrode 6 of an oxygen sensing element 1 is exposed to the exhaust gas. A casing 9 for protecting the oxygen sensing element 1 has a plurality of perforations through which the exhaust gas is allowed to flow. The output signals are transmitted from the respective electrodes through lead-out wires, such as a platinum lead, and to an electrical measuring circuit (not shown in FIGS. 2A and 2B). The output signal-taking out mechanism is electrically protected by an alumina tube 13, a Teflon tube 16 and an insulative tube 12 and is mechanically protected by metallic tubular members 14 and 15.

The invention will be further illustrated by way of the following examples.

EXAMPLE 1

A commercially available carbonyl iron powder, a zirconia powder having incorporated therein 5.5% by mole of $Y_2O_3$ and ammonium bicarbonate were uniformly blended in the proportions shown in Table I, below. One end of a platinum lead-out wire having a diameter of 0.5 mm was inserted into a mass of each of the so obtained blends. Then, each lead-out wire-inserted blend was compression molded into a pellet of a columnar shape by using a hand press at a pressure of 100 kg/cm² for three minutes. The pellet was encapsulated with a $ZrO_2$ powder having incorporated therein 5.5% by mole of $Y_2O_3$. The $ZrO_2$ encapsulated pellet was pressed into a pellet of columnar shape by using a hand press at a pressure of 600 kg/cm² for three minutes. The so obtained pellet was sintered in an electric oven at a temperature of 1,450° C. for three hours while a hydrogen (1% by volume)-argon (99% by volume) gaseous mixture was introduced in the oven at a rate of 1 liter/min. The upper and lower flat surfaces of the sintered columnar pellet were abraded by using a number of 250 abrasive paper and degreased, and then, coated with a platinum paste, as illustrated in FIG. 1. The platinum paste-coated pellet was baked in an electric oven at a temperature of 800° C. for 10 minutes to obtain an oxygen sensing element having external platinum electrodes mounted on the exterior surface thereof.

A contraction in volume of each oxygen sensing element occurred during the sintering, i.e., the ratio, multiplied by 100, of the volume as measured after sintering to the volume as measured before sintering, was about 55%. The operation capability and the appearance of the oxygen sensing elements are shown in Table I, below. The operativeness was evaluated by measuring the electromotive force in an air atmosphere, at a temperature of 500° C., while a load of 20 M-ohm was imparted to the electrode terminals. In Table I, below, "good" and "poor" refer to the fact that the electromotive force was more than 0.8 volt and less than 0.45 volt, respectively.

In order to test the high temperature durability, the above-mentioned evaluation of the operation capability and the appearance was repeated after the oxygen sensing elements were maintained at a temperature of 950° C., in an air atmosphere, over a period of 100 hours, while a load of 1 K-ohm was imparted to the electrode terminals. The evaluated results are shown in Table I, below. This high temperature durability test was continued until the electromotive force of each sensing element decreased below the practically acceptable value. The results are shown in FIG. 3, wherein curves A, B, C, D, E and F correspond to, the specimens A, B, C, D, E and F, in Table I, below.

Table I

| Specimen | Composition of reference solid electrode (wt.%) | | | Volume contraction (%) | Before durability test | | After durability test | |
|---|---|---|---|---|---|---|---|---|
| | Fe | $ZrO_2$ | $NH_4H-CO_3$ | | Operation capability | appearance | Operation capability | apperance |
| A | 100 | 0 | 0 | 55 | *1 | Slightly expanded | Impossible to measure | Cracked |
| B | 75 | 0 | 25 | 55 | Good | Good | Poor | Good |
| C | 65 | 35 | 0 | 55 | Good | Slightly expanded | Poor | Cracked |
| D | 40 | 15 | 45 | 55 | Good | Good | Good | Good |
| E | 50 | 15 | 35 | 55 | Good | Good | Good | Good |
| F | 45 | 10 | 45 | 55 | Good | Good | Good | Good |

*1 There was observed a great variety of operation capability rating from poor to good.

EXAMPLE 2

This example illustrates the effect of a platinum group metal upon the low temperature operation capability of the oxygen sensing element.

By a procedure similar to that mentioned above in Example 1, oxygen sensing elements were manufactured, wherein 2% by weight of a platinum powder and a mixture of 2% by weight of a platinum powder and 0.2% by weight of a rhodium powder, based on the total weight of the respective platinum group metal-incorporated reference solid electrode material, were separately incorporated into each reference solid electrode material of specimens D, E and F. All other conditions remained substantially the same.

Figure 4:
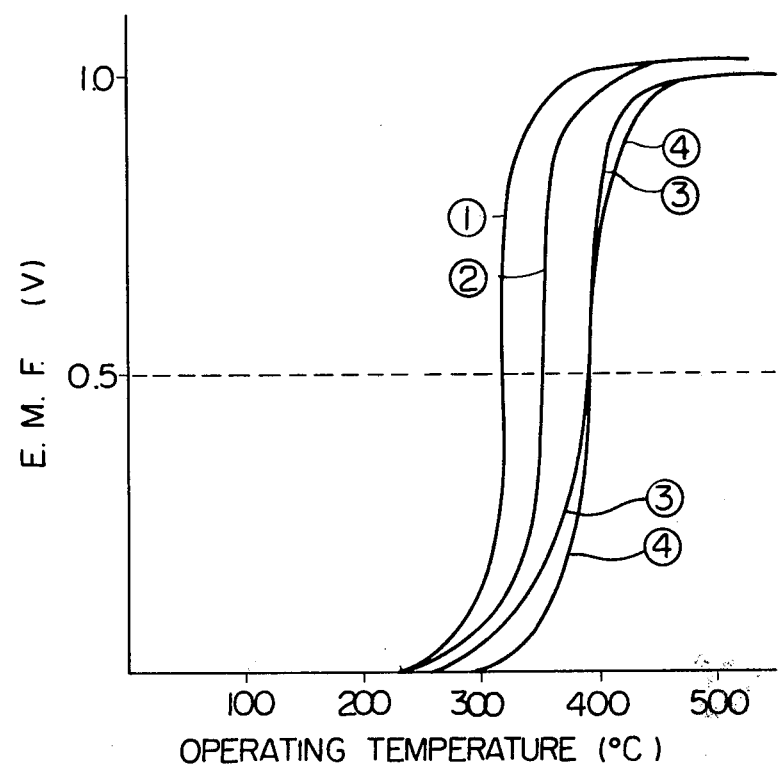
FIG. 4 is a graph showing the dependence of the electromotive force (E.M.F.) of oxygen sensing elements upon the operating temperature.

The dependence of the electromotive force characteristics of the oxygen sensing elements upon the change in temperature were evaluated by elevating the temperature of the air atmosphere, in which sensing element specimens were placed, from room temperature to 500° C., at a rate of 10° C. per minute, while a load of 20 M-ohm was imparted to the electrode terminals. The results obtained on the specimen D, into which the respective platinum group metal powders were separately incorporated, are shown in FIG. 4. In FIG. 4, curves 1, 2 and 3 correspond to the platinum and rhodium-incorporated specimen, the platinum-incorporated specimen, and the specimen having no platinum group metal, respectively. Curve 4 corresponds to a conventional specimen having a structure such that a reference solid electrode material having incorporated therein no platinum group metal is enclosed in a cup-shaped solid electrolyte member and the upper opening of the solid electrolyte member is sealed. Obviously, the low temperature operational capability is successively reduced from curves A to B, B to C and C to D. The results obtained on the other specimens, i.e., specimens E and F, were approximately similar to those shown in FIG. 4.

The air atmosphere temperatures at which the oxygen sensing elements exhibited an electromotive force of 0.5 volt are summarized in Table II, below, from the curves shown in FIG. 4.

Table II

| | Air atmosphere temperatures at which sensing elements exhibited an E.M.F. of 0.5 V (°C.) | |
|---|---|---|
| | Platinum group metal | |
| Specimen | Platinum | Platinum + rhodium |
| D | 393 | 355 | 320 |
| E | 390 | 353 | 326 |
| F | 387 | 348 | 310 |
| Conventional sensor | 395 | — | — |

What we claim is:

1. An improvement in an oxygen sensing element which comprises a solid electrolyte member composed of sintered material, and a means for providing a reference oxygen partial pressure, composed of a sintered product of a finely divided metal or metal-metal oxide powder, said means being completely embedded within the solid electrolyte member and having a lead-out wire connected thereto, and said solid electrolyte member having an electrode or electrodes mounted on the exterior surface thereof, said improvement comprising said finely divided metal or metal-metal oxide powder having dispersed therein an antisintering material and a pore-forming material capable of subliming or being decomposed, thereby to generate gas upon sintering; the amounts of the antisintering material and the pore-forming material being from 5 to 70% by weight and from 20 to 80% by weight, respectively, based on the total weight of the antisintering and pore-forming materials-incorporated metal or metal-metal oxide powder.

2. An oxygen sensing element according to claim 1 wherein said antisintering material is at least one material selected from the group consisting of alumina, alumina-magnesia, silica, alumina-silica and stabilized zirconia.

3. An oxygen sensing element according to claim 1 or 2 wherein the amount of said antisintering material is from 10 to 60% by weight, based on the total weight of the antisintering and pore-forming materials-incorporated metal or metal-metal oxide powder.

4. An oxygen sensing element according to claim 1 wherein said pore-forming material is at least one compound selected from the group consisting of ammonium bicarbonate, naphthalene and camphor.

5. An oxygen sensing element according to claim 1 wherein said finely divided metal or metal-metal oxide powder has dispersed therein, in addition to the antisintering and pore-forming materials, a platinum group metal in an amount of from 0.5 to 10% by weight, based on the total weight of the antisintering and pore-forming materials and platinum group metal-incorporated metal or metal-metal oxide powder.

6. An oxygen sensing element according to claim 5 wherein the platinum group metal is at least one metal selected from the group consisting of platinum, rhodium, palladium and iridium.

7. An oxygen sensor device for determining the oxygen concentration in an exhaust gas from an automobile internal combustion engine, comprising:
   (1) an oxygen sensing element which comprises a solid electrolyte member composed of sintered material, and a means for providing a reference oxygen partial pressure, composed of a sintered product of a finely divided metal or metal-metal oxide power, said means being completely embedded within the solid electrolyte member, said solid electrolyte member having an electrode or electrodes mounted on the external surface thereof, and said finely divided metal or metal oxide powder having dispersed therein an antisintering material and a pore-forming material capable of subliming, boiling or being decomposed, thereby to generate gas upon sintering, the amounts of the antisintering material and the pore-forming material being from 5 to 70% by weight and from 20 to 80% by weight, respectively, based on the total weight of the antisintering and pore-forming materials-incorporated metal or metal-metal oxide powder;
   (2) two lead-out wires for transmitting therethrough output signals from the reference oxygen partial pressure-providing means and the electrode or electrodes on the external surface of the solid electrolyte member, respectively, to an electrical measuring circuit; and,
   (3) a casing for protecting the oxygen sensing element, the casing having a plurality of perforations through which the exhaust gas is allowed to flow.

* * * * *

UNITED STATES PATENT AND TRADEMARK OFFICE
CERTIFICATE OF CORRECTION

PATENT NO. : 4,209,377
DATED : June 24, 1980
INVENTOR(S) : Hiroshi Shinohara, et al It is certified that error appears in the above—identified patent and that said Letters Patent is hereby corrected as shown below:

Col. 3, line 33, change "THe" to --The--.

Col. 7, line 16, change "2B is" to --2B there is--.

Col. 8, Table I, 2nd occurrence, change "ap-erance" to -- ap-pearance --.

Col. 10, line 35, change "power" to --powder--.

Signed and Sealed this

Second Day of December 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,209,377

DATED : June 24, 1980

INVENTOR(S) : Hiroshi Shinohara, et al.

It is certified that error appears in the above—identified patent and that said Letters Patent is hereby corrected as shown below:

Col. 2, line 51, change "manufacturing" to --manufactured--.

Col. 4, line 47, delete "is".

Col. 7, line 10, correct spelling of "combustion".

Col. 7 and Col. 8, Table I, change "Volume contra-ction" to --Volume Contrac-tion--.

Signed and Sealed this

Seventeenth Day of March 1981

[SEAL]

Attest:

RENE D. TEGTMEYER

Attesting Officer     Acting Commissioner of Patents and Trademarks